United States Patent
Chassot et al.

(10) Patent No.: US 7,056,347 B2
(45) Date of Patent: Jun. 6, 2006

(54) COLORING AGENTS FOR KERATIN FIBERS CONTAINING (1,1'-BIPHENYL)-2,4-DIAMINE DERIVATIVES IN ADDITION TO NOVEL (1,1'-BIPHENYL)-2,4-DIAMINE-DERIVATIVES

(75) Inventors: Laurent Chassot, Praroman (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 384 days.

(21) Appl. No.: 10/240,555

(22) PCT Filed: Sep. 10, 2001

(86) PCT No.: PCT/EP01/10409

§ 371 (c)(1),
(2), (4) Date: Apr. 29, 2003

(87) PCT Pub. No.: WO02/062307

PCT Pub. Date: Aug. 15, 2002

(65) Prior Publication Data

US 2003/0172470 A1    Sep. 18, 2003

(30) Foreign Application Priority Data

Feb. 2, 2001    (DE) .................. 101 04 770

(51) Int. Cl.
*A61K 7/13*    (2006.01)
(52) U.S. Cl. ............... 8/405; 8/406; 8/410; 8/411; 8/415; 8/421
(58) Field of Classification Search ............ 8/405, 8/406, 410, 411, 415, 421
See application file for complete search history.

(56) References Cited

U.S. PATENT DOCUMENTS

| | | | |
|---|---|---|---|
| 2,926,060 A | * 2/1960 | Lehmann et al. | 8/611 |
| 3,619,399 A | 11/1971 | Blank | 204/181 |
| 5,368,610 A | * 11/1994 | Chan et al. | 8/406 |
| 5,376,146 A | * 12/1994 | Casperson et al. | 8/408 |
| 5,393,305 A | * 2/1995 | Cohen et al. | 8/406 |
| 5,542,953 A | * 8/1996 | Balzer et al. | 8/416 |
| 5,849,041 A | * 12/1998 | Kunz et al. | 8/408 |

FOREIGN PATENT DOCUMENTS

| | | | |
|---|---|---|---|
| DE | 1176318 | * | 8/1964 |
| DE | 22 32 095 A | | 1/1974 |
| DE | 2232095 A | * | 1/1974 |
| DE | 30 28 131 | | 2/1981 |
| GB | 1 425 064 A | | 2/1976 |
| WO | 99 59527 A | | 11/1999 |

OTHER PUBLICATIONS

S. Arvamuthan et al. (Electrochemical reduction of 2,3'-dinitrobenzene in buffered aqueous methanol), XP-001073817, Feb. 15, 1989.*
STIC Search Report dated Mar. 31, 2005.*
S. Aravamuthan et al: "Electrichemical Reduction of 2,3 . . . " Journal of Applied Electrochemistry, Bd. 19, Nr. 6, 1989, pp. 897-900.

* cited by examiner

*Primary Examiner*—Eisa Elhilo
(74) *Attorney, Agent, or Firm*—Michael J. Striker

(57) ABSTRACT

Keratin fiber coloring agents containing (1,1'-biphenyl)-2,4-diamine derivatives of general formula (I) or a physiologically tolerated salt thereof

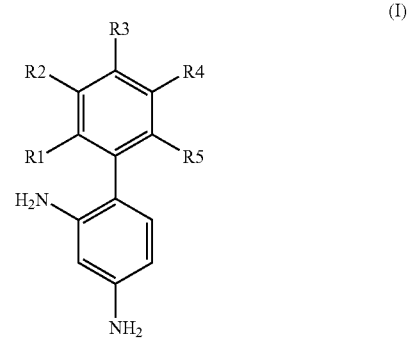

and novel (1,1'-biphenyl)-2,4-diamine derivatives.

11 Claims, No Drawings

COLORING AGENTS FOR KERATIN FIBERS CONTAINING (1,1'-BIPHENYL)-2,4-DIAMINE DERIVATIVES IN ADDITION TO NOVEL (1,1'-BIPHENYL)-2,4-DIAMINE-DERIVATIVES

BACKGROUND OF THE INVENTION

1. Field of the Invention.

The present invention relates to agents for oxidative dyeing of keratin fibers, particularly human hair, based on a developer/coupler combination which contains a (1,1'-biphenyl)-2,4-diamine derivative as the coupler, and to new (1,1'-biphenyl)-2,4-diamine derivatives.

2. Description of the Related Art.

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 4,5-diamino-1-(2'-hydroxyethyl)pyrazole and 1,4-diamino-benzene, and suitable couplers are, for example, resorcinol, 2-methylresorcinol, 1-naphthol, 3-aminophenol, m-phenylenediamine, 2-amino-4-(2'-hydroxyethyl)amino-anisole, 1,3-diamino-4-(2'-hydroxyethoxy)benzene and 2,4-diamino-5-fluorotoluene.

The oxidation dyes used for dyeing human hair must meet numerous requirements in addition to that of being able to produce colorations of the desired intensity. For example, these dyes must be harmless from a toxicological and dermatological standpoint, and the hair colorations obtained must have good light fastness, resistance to permanent waving, acid fastness and rubbing fastness. In any case, however, in the absence of exposure to light, rubbing and chemicals, such colorations must remain stable over a period of at least 4 to 6 weeks. Moreover, by combining appropriate developers and couplers, it must be possible to create a wide range of different color shades.

Attempts have already been made to improve the properties of m-phenylenediamines by introduction of substituents. In this regard, the reader is referred to German Unexamined Patent Application DE 30 28 131 which, among other things, also describes dyeing agents which as couplers contain special m-phenylenediamines alkyl-substituted in the 4-position.

With the currently known dyeing agents, however, it is not possible to meet the requirements placed on such agents in all respects. Hence, the need continued to exist for novel couplers that would meet the aforesaid requirements to a particularly high degree.

SUMMARY OF THE INVENTION

We have now found that by use of (1,1'-biphenyl)-2,4-diamine derivatives of general formula (I) intense, stable blue color shades can be obtained in addition to natural and purple or violet shades.

Hence, the object of the present invention is an agent for oxidative dyeing of keratin fibers, for example wool, furs, feathers or hair, particularly human hair, which agent is based on a developer-coupler combination that is characterized by the fact that it contains as the coupler at least one (1,1'-biphenyl)-2,4-diamine derivative of formula (I) or a physiologically tolerated salt thereof

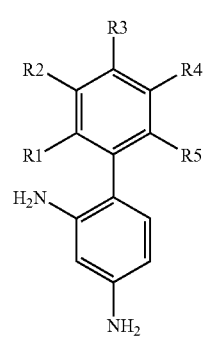

wherein
R1, R2, R3, R4 and R5 can be equal or different and independently of each other denote hydrogen, a halogen atom (fluorine, chlorine, bromine, iodine), a cyano group, a hydroxyl group, a $C_1$–$C_4$-alkoxy group, a $C_1$–$C_4$-hydroxyalkoxy group. a $C_1$–$C_6$-alkyl group, a $C_1$–$C_4$-alkyl thioether group, a mercapto group, a nitro group, an amino group ($NH_2$), a $C_1$–$C_4$-monoalkylamino group, a di($C_1$–$C_4$)-alkylamino group, a trifluoromethyl group, a —C(O)H group, a —C(O)$CH_3$ group, a —C(O)$CF_3$ group, an —Si($CH_3$)$_3$ group, a $C_1$–$C_4$-hydroxyalkyl group, a $C_2$–$C_4$-dihydroxyalkyl group, a —CH=CHR6 group, a —($CH_2$)$_p$—$CO_2$R7 group or a —($CH_2$)$_p$—R8 group with p=1, 2, 3 or 4, a —C(R9)=NR10 group or a C(R12)H—NR13R14 group, or two adjacent R1 to R5 groups form an —O—$CH_2$—O bridge;
R6 denotes hydrogen, a nitro group, a $CO_2$R7 group or a —C(O)$CH_3$ group;
R7, R9 and R12 can be equal or different and independently of each other denote hydrogen or a $C_1$–$C_4$-alkyl group;
R8 denotes an amino or nitrile group;
R10, R13 and R14 can be equal or different and independently of each other denote hydrogen, a hydroxyl group, a $C_1$–$C_4$-alkyl group, a $C_1$–$C_4$-hydroxyalkyl group, a $C_2$–$C_4$-dihydroxyalkyl group or a group of formula

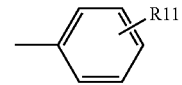

and R11 denotes hydrogen, an amino group or a hydroxyl group.

Noteworthy among the compounds of formula (I) are, for example:
biphenyl-2,4-diamine; 4-benzo[1,3]dioxol-5-ylbenzene-1,3-diamine; 2'-(2-hydroxyethyl)biphenyl-2,4-diamine; 2'-acetylbiphenyl-2,4-diamine; 2'-aminobiphenyl-2,4-diamine; 2'-bromobiphenyl-2,4-diamine; 2'-chlorobiphenyl-2,4-diamine; 2'-cyanobiphenyl-2,4-diamine; 2'-ethylbiphenyl-2,4-diamine; 2'-fluorobiphenyl-2,4-diamine; 2'-hydroxybiphenyl-2,4-diamine; 2'-methoxybiphenyl-2,4-diamine; 2'-methylbiphenyl-2,4-diamine; 2'-methylsulfanylbiphenyl-2,4-diamine; 2'-nitrobiphenyl-2,4-diamine; 2'-trifluoromethylbiphenyl-2,4-diamine; 3'-(2-hydroxyethyl)biphenyl-2,4-diamine; 3'-acetylbiphenyl-2,4-diamine; 3'-aminobiphenyl-2,4-diamine; 3'-bromobiphenyl-2,4-diamine; 3'-chlorobiphenyl-2,4-diamine; 3'-cyanobiphenyl-2,4-diamine; 3'-ethylbiphenyl-2,4-diamine; 3'-fluorobiphenyl-2,4-diamine; 3'-hydroxybiphenyl-2,4-diamine; 3'-methoxybiphenyl-2,4-diamine; 3'-methylbiphenyl-2,4-diamine; 3'-methylsulfanylbiphenyl-2,4-diamine; 3'-nitrobiphenyl-2,4-diamine; 3'-trifluoromethylbiphenyl-2,4-diamine; 4'-(2-hydroxyethyl)biphenyl-2,4-diamine; 4'-acetylbiphenyl-2,4-diamine; 4'-aminobiphenyl-2,4-diamine; 4'-bromobiphenyl-2,4-diamine; 4'-chlorobiphenyl-2,4-diamine; 4'-cyanobiphenyl-2,4-diamine; 4'-ethylbiphenyl-2,4-diamine; 4'-fluorobiphenyl-2,4-diamine; 4'-hydroxybiphenyl-2,4-diamine; 4'-methoxybiphenyl-2,4-diamine; 4'-methylbiphenyl-2,4-diamine; 4'-methylsulfanylbiphenyl-2,4-diamine; 4'-nitrobiphenyl-2,4-diamine; 4'-trifluoromethylbiphenyl-2,4-diamine; 2'-amino-3'-aminobiphenyl-2,4-diamine; 2'-amino-3'-hydroxybiphenyl-2,4-diamine; 2'-amino-3'-methoxybiphenyl-2,4-diamine; 2'-amino-3'-methylbiphenyl-2,4-diamine; 2'-amino-4'-aminobiphenyl-2,4-diamine; 2'-amino-4'-hydroxybiphenyl-2,4-diamine; 2'-amino'-4'-methoxybiphenyl-2,4-diamine; 2'-amino-4'-methylbiphenyl-2,4-diamine; 2'-amino-5'-aminobiphenyl- 2,4-diamine; 2'-amino-5'-hydroxybiphenyl-2,4-diamine; 2'-amino-5'-methoxybiphenyl-2,4-diamine; 2'-amino-5'-methylbiphenyl-2,4-diamine; 2'-amino-6'-aminobiphenyl-2,4-diamine; 2'-amino-6'-hydroxybiphenyl-2,4-diamine; 2'-amino-6'-methoxybiphenyl-2,4-diamine; 2'-amino-6'-methylbiphenyl-2,4-diamine; 2'-hydroxy-3'-aminobiphenyl-2,4-diamine; 2'-hydroxy-3'-hydroxybiphenyl-2,4-diamine; 2'-hydroxy-3'-methoxybiphenyl-2,4-diamine; 2'-hydroxy-3'-methylbiphenyl-2,4-diamine; 2'-hydroxy-4'-aminobiphenyl-2,4-diamine; 2'-hydroxy-4'-hydroxybiphenyl-2,4-diamine; 2'-hydroxy-4'-methoxybiphenyl-2,4-diamine; 2'-hydroxy-4'-methylbiphenyl-2,4-diamine; 2'-hydroxy-5'-aminobiphenyl-2,4-diamine; 2'-hydroxy-5'-hydroxybiphenyl-2,4-diamine; 2'-hydroxy-5'-methoxybiphenyl-2,4-diamine; 2'-hydroxy-5'-methylbiphenyl-2,4-diamine; 2'-hydroxy-6'-aminobiphenyl-2,4-diamine; 2'-hydroxy-6'-hydroxybiphenyl-2,4-diamine; 2'-hydroxy-6'-methoxybiphenyl-2,4-diamine; 2'-hydroxy-6'-methylbiphenyl-2,4-diamine; 2'-methoxy-3'-aminobiphenyl-2,4-diamine; 2'-methoxy-3'-hydroxybiphenyl-2,4-diamine; 2'-methoxy-3'-methoxybiphenyl-2,4-diamine; 2'-methoxy-3'-methylbiphenyl-2,4-diamine; 2'-methoxy-4'-aminobiphenyl-2,4-diamine; 2'-methoxy-4'-hydroxybiphenyl-2,4-diamine; 2'-methoxy-4'-methoxybiphenyl-2,4-diamine; 2'-methoxy-4'-methylbiphenyl-2,4-diamine; 2'-methoxy-5'-aminobiphenyl-2,4-diamine; 2'-methoxy-5'-hydroxybiphenyl-2,4-diamine; 2'-methoxy-5'-methoxybiphenyl-2,4-diamine; 2'-methoxy-5'-methylbiphenyl-2,4-diamine; 2'-methoxy-6'-aminobiphenyl-2,4-diamine; 2'-methoxy-6'-hydroxybiphenyl-2,4-diamine; 2'-methoxy-6'-methoxybiphenyl-2,4-diamine; 2'-methoxy-6'-methylbiphenyl-2,4-diamine; 2'-methyl-3'-aminobiphenyl-2,4-diamine; 2'-methyl-3'-hydroxybiphenyl-2,4-diamine; 2'-methyl-3'-methoxybiphenyl-2,4-diamine; 2'-methyl-3'-methylbiphenyl-2,4-diamine; 2'-methyl-4'-aminobiphenyl-2,4-diamine; 2'-methyl-4'-hydroxybiphenyl-2,4-diamine; 2'-methyl-4'-methoxybiphenyl-2,4-diamine; 2'-methyl-4'-methylbiphenyl-2,4-diamine; 2'-methyl-5'-aminobiphenyl-2,4-diamine; 2'-methyl-5'-hydroxybiphenyl-2,4-diamine; 2'-methyl-5'-methoxybiphenyl-2,4-diamine; 2'-methyl-5'-methylbiphenyl-2,4-diamine; 2'-methyl-6'-aminobiphenyl-2,4-diamine; 2'-methyl-6'-hydroxybiphenyl-2,4-diamine; 2'-methyl-6'-methoxybiphenyl-2,4-diamine; 2'-methyl-6'-methylbiphenyl-2,4-diamine; 3'-amino-4'-aminobiphenyl-2,4-diamine; 3'-amino-4'-hydroxybiphenyl-2,4-diamine; 3'-amino-4'-methoxybiphenyl-2,4-diamine; 3'-amino-4'-methylbiphenyl-2,4-diamine; 3'-amino-5'-aminobiphenyl-2,4-diamine; 3'-amino-5'-hydroxybiphenyl-2,4-diamine; 3'-amino-5'-methoxybiphenyl-2,4-diamine; 3'-amino-5'-methylbiphenyl-2,4-diamine; 3'-hydroxy-4'-aminobiphenyl-2,4-diamine; 3'-hydroxy- 4'-hydroxy-biphenyl-2,4-diamine; 3'-hydroxy-4'-methoxybiphenyl-2,4-diamine; 3'-hydroxy-4'-methylbiphenyl-2,4-diamine; 3'-hydroxy-5'-aminobiphenyl-2,4-diamine; 3'-hydroxy-5'-hydroxybiphenyl-2,4-diamine; 3'-hydroxy-5'-methoxybiphenyl-2,4-diamine; 3'-hydroxy-5'-methylbiphenyl-2,4-diamine; 3'-methoxy-4'-aminobiphenyl-2,4-diamine; 3'-methoxy-4'-hydroxybiphenyl-2,4-diamine; 3'-methoxy-4'-methoxybiphenyl-2,4-diamine; 3'-methoxy-4'-methylbiphenyl-2,4-diamine; 3'-methoxy-5'-aminobiphenyl-2,4-diamine; 3'-methoxy-5'-hydroxybiphenyl-2,4-diamine; 3'-methoxy-5'-methoxybiphenyl-2,4-diamine; 3'-methoxy-5'-methylbiphenyl-2,4-diamine; 3'-methyl-4'-aminobiphenyl-2,4-diamine; 3'-methyl-4'-hydroxybiphenyl-2,4-diamine; 3'-methyl-4'-methoxybiphenyl-2,4-diamine; 3'-methyl-4'-methylbiphenyl-2,4-diamine; 3'-methyl-5'-aminobiphenyl-2,4-diamine; 3'-methyl-5'-hydroxybiphenyl-2,4-diamine; 3'-methyl-5'-methoxybiphenyl-2,4-diamine and 3'-methyl-5'-methylbiphenyl-2,4-diamine, as well as the physiologically tolerated salts thereof.

Preferred compounds of formula (I) or their physiologically tolerated salts are those wherein (i) at least three of the R1 to R5 groups denote hydrogen or (ii) three of the R1 to R5 groups denote hydrogen and the two remaining groups independently of each other denote hydrogen, a methoxy group, a hydroxyl group, a $C_1$–$C_4$-alkyl group, a $C_1$–$C_4$-hydroxyalkyl group or an amino group, or when the two remaining groups are adjacent to each other they together form an —O—$CH_2$—O— bridge.

Particularly preferred are the following (1,1'-biphenyl)-2,4-diamine derivatives of formula (I): biphenyl-2,4-diamine; 4-benzo[1,3]dioxol-5-ylbenzene-1,3-diamine; 4'-hydroxybiphenyl-2,4-diamine; 4'-aminobiphenyl-2,4-diamine; 3'-hydroxybiphenyl-2,4-diamine; 4'-methoxybiphenyl-2,4-diamine and the physiologically tolerated salts thereof.

The compounds of formula (I) can be used as the free bases as well as in the form of their physiologically tolerated salts with inorganic or organic acids, for example hydrochloric acid, sulfuric acid, phosphoric acid, acetic acid, propionic acid, lactic acid or citric acid.

The colorant of the invention contains the (1,1'-biphenyl)-2,4-diamine derivatives of formula (I) in a total amount from about 0.005 to 20 wt. %, an amount of about 0.01 to 5 wt. % and especially 0.1 to 2.5 wt. % being preferred.

Suitable developers are all those developers that are known to be used with, and are appropriate for, such colorants, for example 1,4-diaminobenzene (p-phenylenediamine), 1,4-diamino-2-methylbenzene (p-toluylenediamine), 1,4-diamino-2,6-dimethylbenzene, 1,4-diamino-3, 5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl; 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 1-(2,5-diaminophenyl)ethanol, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(2-hydroxyethyl)benzene, 1,4-diamino-2-(1-methylethyl)benzene, 1,3-bis-[(4-aminophenyl)(2-hydroxyethyl)amino]-2-propanol, 1,4-bis-[(4-aminophenyl)amino]butane, 1,8-bis-(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]-methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-methyl-1H-pyrazole, 4,5-diamino-3-methyl-1-methyl-1H-pyrazole[sic-Translator], 2-aminophenol, 2-amino-6-methylphenol and 2-amino-5-methylphenol.

Moreover, the colorant of the invention can optionally also contain other known couplers, for example 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 2-(4-amino-2-hydroxyphenoxy)-ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-di-hydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

The couplers and developers can be present in the colorant of the invention either individually or in admixture with one another, the total amount of each of the couplers and developers in the colorant of the invention being about 0.005 to 20 wt. % preferably about 0.01 to 5.0 wt. % and particularly 0.1 to 2.5 wt. % (based on the total amount of colorant). The total amount of the developer-coupler combination contained in the colorant described herein is preferably about 0.01 to 20 wt. %, an amount of about 0.02 to 10 wt. % and especially 0.2 to 6 wt. % being particularly preferred. In general, the developer and the coupler are used in approximately equimolar amounts. In this respect, it is not disadvantageous, however, if the developer is present in a certain excess or deficiency [for example in a (coupler: developer) ratio of 1:2 to 1:0.5].

Moreover, the colorant of the invention can also contain other dye components, for example 6-amino-2-methylphenol and 2-amino-5-methylphenol, as well as common anionic, cationic, amphoteric or nonionic direct dyes, for example triphenylmethane dyes such as 4-[(4'-aminophenyl)-(4'-imino-2",5"-cyclohexadien-1"-ylidene)methyl]-2-methylaminobenzene monohydrochloride (Color Index [C.I.]42 510) and 4-[(4'-amino-3'-methylphenyl)-(4"-imino-3"-methyl-2",5"-cyclohexadien-1"-ylidene)methyl]-2-methylaminobenzene monohydrochloride (C.I. 42 520), aromatic nitro dyes such as 4-(2'-hydroxyethyl)aminonitrotoluene, 2-amino-4,6-dinitrophenol, 2-amino-5-(2'-hydroxyethyl)aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-(2'-ureidoethyl)amino-4-nitrobenzene, azo dyes such as, for example, sodium 6-[(4'-aminophenyl)azo]-5-hydroxynaphthalene-1-sulfonate (C.I. 14 805) and disperse dyes, for example 1,4-diaminoanthraquinone and 1,4,5,8-tetraaminoanthraquinone. The colorants of the invention can contain the aforesaid dye components in an amount from about 0.1 to 4 wt. %.

The couplers and developers as well as the other dye components, provided they are bases, can, of course, also be used in the form of their physiologically tolerated salts with organic or inorganic acids, for example hydrochloric acid or sulfuric acid, or—if they contain aromatic OH groups—in the form of their salts with bases, for example as alkali metal phenoxides.

Moreover, if the colorants of the invention are to be used for coloring hair, they can also contain other common cosmetic additives, for example antioxidants such as ascorbic acid, thio-glycolic acid or sodium sulfite, as well as perfume oils, complexing agents, wetting agents, emulsifiers, thickeners and hair-care agents.

The colorant of the invention can be in the form of, for example, a solution, particularly an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The said constituents are used in amounts commonly employed for such purposes, for example the wetting agents and emulsifiers at a concentration of about 0.5 to 30 wt. %, the thickeners in an amount from about 0.1 to 25 wt. % and the hair-care agents at a concentration from about 0.1 to 5 wt. %.

Depending on the composition, the colorant of the invention can be weakly acidic, neutral or alkaline. In particular, it has a pH of 6.5 to 11.5. Adjustment to a basic pH is preferably done with ammonia, but it can also be done with an organic amine, for example monoethanolamine and triethanolamine, or with an inorganic base such as sodium hydroxide and potassium hydroxide. Suitable for adjustment to an acidic pH are inorganic or organic acids, for example phosphoric acid, acetic acid, citric acid or tartaric acid.

For oxidative dyeing of hair, the afore-described colorant is mixed with an oxidant just before use, and the resulting mixture is applied to hair in an amount sufficient for the hair-dyeing treatment, in general about 50 to 200 grams, depending on the hair fullness. The ready-to-use oxidative hair colorant obtained after mixing with the oxidant preferably has a pH of 6.5 to 11.5.

Suitable oxidants for developing the hair coloration are mainly hydrogen peroxide or its products of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from 5:1 to 1:2, but preferably 1:1. Larger amounts of oxidant are used primarily at higher dye concentrations in the hair colorant or when stronger bleaching of the hair is wanted at the same time. The mixture is allowed to act on the hair at 15 to 50° C. for about 10 to 45 min, preferably 30 min, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing a (1,1'-biphenyl)-2,4-diamine derivative of formula (I) as coupler give hair colorations of excellent color stability, particularly in terms of light fastness, wash fastness and rubbing fastness. As far as the dyeing properties are concerned, the hair colorants of the invention provide a wide range of different color shades from blond to brown, purple, violet and even blue and black, depending on the developer-coupler combination used, the achievable intense and stable blue shades being particularly noteworthy. The very good coloring properties of the hair colorant of the present patent application also manifest themselves in that this colorant makes it possible to dye gray hair, previously not damaged chemically, without any problems and with good covering power.

The (1,1'-biphenyl)-2,4-diamine derivatives of formula (I) can be prepared by known methods of synthesis, for example by methods similar to those described in the practical examples given hereinbelow.

The (1,1'-biphenyl)-2,4-diamine derivatives of formula (I) are highly water-soluble and give colorations—particularly in the blue and purple color range—of high color intensity and excellent color stability, particularly in terms of light fastness, wash fastness and rubbing fastness. Moreover, they have excellent storage stability, particularly as constituents of the oxidation colorants described herein.

Hence, another object of the present invention are (1,1'-biphenyl)-2,4-diamine derivatives of general formula (II)

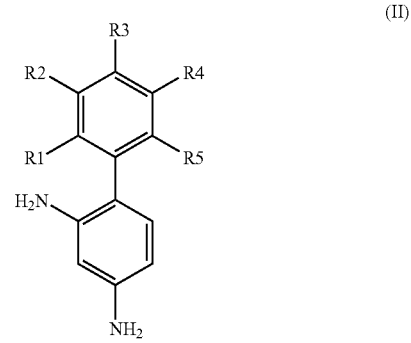

(II)

wherein

R1, R2, R3, R4, R5 can be equal or different and independently of each other denote hydrogen, hydrogen[sic-Translator], a chlorine atom, a fluorine atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group ($NH_2$), a $C_1$–$C_4$-monoalkylamino group, a di($C_1$–$C_4$)-alkylamino group, a trifluoromethyl group, a —C(O)H group, a —C(O)$CH_3$ group, a —C(O)$CF_3$ group, an —Si$(CH_3)_3$ group, a $C_1$–$C_4$-hydroxyalkyl group, a $C_2$–$C_4$-dihydroxyalkyl group, a —CH=CHR6 group, a —$(CH_2)_p$—$CO_2$R7 group, a —$(CH_2)_p$—R8 group with p=1, 2, 3 or 4, a —C(R9)=NR10 group or a C(R12)H—NR13R14 group, or two adjacent R1 to R5 groups form an —O—$CH_2$O— bridge;

R6 denotes hydrogen, a nitro group, a $CO_2$R7 group or a —C(O)$CH_3$ group;

R7, R9 and R12 can be equal or different and independently of each other denote hydrogen or a $C_1$–$C_4$-alkyl group;

R8 denotes an amino group or a nitrile group;

R10, R13 and R14 can be equal or different and independently of each other denote hydrogen, a hydroxyl group, a $C_1$–$C_4$-alkyl group, a $C_1$–$C_4$-hydroxyalkyl group, a $C_2$–$C_4$-dihydroxyalkyl group or a group having the formula

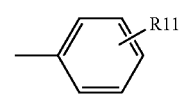

and R11 denotes hydrogen, an amino group or a hydroxyl group;

and at least one of the R1 to R5 groups does not denote hydrogen, or the physiologically tolerated salts thereof.

The following examples illustrate the object of the invention in greater detail without limiting its scope.

EXAMPLES

Example 1

A. Synthesis of tert.butyl(4-bromo-3-tert.butoxycarbonylaminophenyl)carbamate

To a suspension of 10 g (32.4 mmoles) of tert.butyl(3-tert.butoxycarbonylaminophenyl)carbamate in 100 mL of 1,2-dimethoxyethane was added dropwise at 0° C. over a period of 2 hours a solution of 6 g (33.7 mmoles) of N-bromosuccinimide in 50 mL of 1,2-dimethoxyethane. The reaction mixture was then allowed to agitate for an additional 2 hours. At the end of the reaction, the reaction mixture was poured into 300 mL of water which produced a precipitate. The precipitate was filtered off and washed with water.

This gave 11 g (94% of the theoretical) of tert.butyl(4-bromo-3-tert.butoxycarbonylaminophenyl)carbamate.

$^1$H-NMR (300 MHz, DMSO-D6): δ=9.51 (s, 1H); 8.43 (s, 1H); 7.89 (s, 1H); 7.47 (d, 1H); 7.18 (d, 1H); 1.47 (d, 18H).

B. Synthesis of tert.butyl[3-tert.butoxycarbonylamino-4-(4,4,5,5-tetramethyl-[1,3,2]dioxa-2-borolanyl)phenyl]carbamate 210 mL of degassed dioxane was added under argon to a mixture of 7.8 g (20.2 mmoles) of tert.butyl(4-bromo-3-tert.butoxycarbonylaminophenyl)carbamate from step A, 12.8 g (50.6 mmoles) of 4,4,4',4',5,5,5,5'-octamethyl[2,2'] bi{[1,3,2]-dioxaborinanyl}, 2 g (2.9 mmoles) of dichloro-[1,1'-bis(diphenylphosphino)ferrocene] palladium[PdCl$_2$ (dppf)] and 6.2 g (63.2 mmoles) of potassium acetate. The mixture was allowed to agitate 26 hours at 80° C. and to it was then added a mixture of 4.2 g (16.9 mmoles) of diboronpinacole ester and 700 mg (0.95 mmole) of PdCl$_2$ (dppf). The reaction mixture was then allowed to agitate for an additional 14 hours at 80° C. after which it was poured into water and extracted with ethyl acetate. The organic phase was washed with a saturated aqueous sodium chloride solution, dried over sodium sulfate and filtered, and the filtrate was evaporated. The resulting crude product was purified on deactivated silica gel with hexane/ethyl acetate (1:1).

This gave 6.20 g (71% of the theoretical) of tert.butyl[3-tert.butoxycarbonylamino-4-(4,4,5,5-tetramethyl[1,3,2]dioxa-2-borolanyl)phenyl]carbamate.

C. Synthesis of (1,1'-biphenyl)-2,4-diamines 0.09 g (0.0002 mole) of tert.butyl[3-tert.butoxycarbonylamino-4-(4,4,5,5-tetramethyl-[1,3,2]dioxa-2-borolanyl) phenyl]carbamate from step B and 0.0004 mole of the appropriate bromo derivative were dissolved in 10 mL of 1,2-dimethoxyethane under argon. Then, 0.01 g (0.000005 mole) of tetrakis(triphenylphosphine)palladium and 0.26 mL of 2N potassium carbonate solution were added, and the reaction mixture was heated to 80° C. At the end of the reaction, the reaction mixture was poured into 10 mL of ethyl acetate and the organic phase was extracted with dilute sodium hydroxide and dried with magnesium sulfate. The solvent was distilled off in a rotary evaporator, and the residue was purified on silica gel with petroleum ether/ethyl acetate (9:1). The resulting product in 4 mL of ethanol was heated to 50° C. Then, to prepare the hydrochloride, 1.5 mL of a 2.9 molar ethanolic hydrochloric acid solution was added dropwise. The precipitate was filtered off, washed twice with 1-mL portions of ethanol and dried.

a. Biphenyl-2,4,4'-triamine hydrochloride
   Bromo derivative used: 4-bromoaniline
   Mass spectrum: MH$^+$ 200 (100)
b. 2',4'-Diaminobiphenyl-4-ol hydrochloride
   Bromo derivative used: 4-bromophenol
   Mass spectrum: MH$^+$ 201 (15)
c. 2',4'-Diaminobiphenyl-3-ol hydrochloride
   Bromo derivative used: 3-bromophenol
   Mass spectrum: MH$^+$ 201 (40)
d. Biphenyl-2,4-diamine hydrochloride
   Bromo derivative used: 4-bromobenzene
   Mass spectrum: MH$^+$ 185 (100)
e. 3'-Methoxybiphenyl-2,4-diamine hydrochloride
   Bromo derivative used: 3-bromoanisole
   Mass spectrum: MH$^+$ 215 (60)
f. 4-Benzo[1,3]dioxol-5-ylbenzene-1,3-diamine hydrochloride
   Bromo derivative used: 5-bromobenzo[1,3]dioxol
   Mass spectrum: MH$^+$ 229 (90)
g. 4'-Methylbiphenyl-2,4-diamine hydrochloride
   Bromo derivative used: 4-bromotoluene
   Mass spectrum: MH$^+$ 199 (100)
h. 4'-Fluorobiphenyl-2,4-diamine hydrochloride
   Bromo derivative used: 4-fluoro-1-bromobenzene
   Mass spectrum: MH$^+$ 23 (100)
i. 2',4'-Diaminobiphenyl-4-carbonitrile hydrochloride
   Bromo derivative used: 4-bromobenzonitrile
   Mass spectrum: MH$^+$ 210 (15)
j. 1-(2',4'-Diaminobiphenyl-3-yl)ethanone hydrochloride
   Bromo derivative used: 3-bromoacetophenone
   Mass spectrum: MH$^+$ 227 (60)
k. 4'-Nitrobiphenyl-2,4-diamine hydrochloride
   Bromo derivative used: 4-bromonitrobenzene
   Mass spectrum: MH$^+$ 230 (100)
l. 2'-Nitrobiphenyl-2,4-diamine hydrochloride
   Bromo derivative used: 2-bromonitrobenzene
   Mass spectrum: MH$^+$ 230 (100)
m. 4'-Trifluoromethylbiphenyl-2,4-diamine hydrochloride
   Bromo derivative used: 4-bromotrifluoromethylbenzene
   Mass spectrum: MH$^+$ 253 (20)
n. 2',4'-Dimethylbiphenyl-2,4-diamine hydrochloride
   Bromo derivative used: 2-bromo-m-xylene
   Mass spectrum: MH$^+$ 213 (60)
4'-Chlorobiphenyl-2,4-diamine hydrochloride
   Bromo derivative used: 4-bromochlorobenzene
   Mass spectrum: MH$^+$ 219 (28)
p. 4'-Methylsulfanylbiphenyl-2,4-diamine hydrochloride
   Bromo derivative used: 1-bromo-4-methylsulfanylbenzene
   Mass spectrum: MH$^+$ 231 (18)

Examples 2 to 17

Hair Colorants

Hair colorant solutions having the following composition were prepared:

| | |
|---|---|
| 1.25 mmoles | of coupler of formula (I) as per Table 1 |
| 1.25 mmoles | of developer according to Table 1 |
| 1.0 g | of potassium oleate (8% aqueous solution) |
| 1.0 g | of ammonia (22% aqueous solution) |
| 1.0 g | of ethanol |

-continued

| | |
|---|---|
| 0.3 g | of ascorbic acid |
| to 100.0 g | water |

Just before use, 50 g of the foregoing coloring solution was mixed with 50 g of a 6% aqueous hydrogen peroxide solution. The mixture was then applied to bleached hair. After an exposure time of 30 min at 40° C., the hair was rinsed with water, washed with a commercial shampoo and dried. The resulting color shades are presented in Table 1.

TABLE 1

| | | Developer | | | |
|---|---|---|---|---|---|
| Example No. | Coupler of formula (I) | I. 1,4-Di-amino-benzene | II. 2,5-Diamino-toluene sulfate | III. 2,5-Diamino-phenyletha-nol sulfate | IV. 4,5-Diamino-1-(2'-hydroxyeth-yl)pyrazole sulfate |
| 2 | As per Ex. 1a | dark blue | dark blue | dark blue | purple |
| 3 | As per Ex. 1b | dark blue | dark blue | dark blue | purple |
| 4 | As per Ex. 1c | dark blue | dark blue | dark blue | purple |
| 5 | As per Ex. 1d | dark blue | blue | dark blue | purple |
| 6 | As per Ex. 1e | dark blue | dark blue | dark blue | purple |
| 7 | As per Ex. 1f | dark blue | dark blue | dark blue | purple |
| 8 | As per Ex. 1g | dark blue | dark blue | blue | purple |
| 9 | As per Ex. 1h | dark blue | dark blue | blue | purple |
| 10 | As per Ex. 1i | dark blue | blue | blue | purple |
| 11 | As per Ex. 1j | dark blue | blue | blue | purple |
| 12 | As per Ex. 1k | dark blue | blue | blue | purple |
| 13 | As per Ex. 1l | dark blue | blue | blue | purple |
| 14 | As per Ex. 1m | dark blue | blue | blue | purple |
| 15 | As per Ex. 1n | dark blue | blue | blue | purple |
| 16 | As per Ex. 1o | dark blue | blue | blue | purple |
| 17 | As per Ex. 1p | dark blue | blue | blue | purple |

Examples 18 to 41

Hair Colorants

Hair colorant solutions of the following composition were prepared:

| | |
|---|---|
| X g | of (1,1'-biphenyl)-2,4-diamine [coupler K1 to K4 of formula (I) as per Table 4] |
| U g | of developer E8 to E15 as per Table 2 |
| Y g | of coupler K11 to K36 as per Table 4 |
| Z g | of direct dye D1 to D3 as per Table 3 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. Table 5 shows the coloring results.

TABLE 2

| Developers | |
|---|---|
| E8 | 1,4-diaminobenzene |
| E9 | 2-(2,5-diaminophenyl)ethanol sulfate |

TABLE 2-continued

| Developers | |
|---|---|
| E10 | 3-methyl-4-aminophenol |
| E11 | 4-amino-2-aminomethylphenol dihydrochloride |
| E12 | 4-aminophenol |
| E13 | N,N-bis(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

| Direct Dyes | |
|---|---|
| D1 | 2,6-diamino-3-[(3-pyridinyl)azo]pyridine |
| D2 | 6-chloro-2-ethylamino-4-nitrophenol |
| D3 | 2-amino-6-chloro-4-nitrophenol |

TABLE 4

| Couplers | |
|---|---|
| K1 | biphenyl-2,4,4'-triamine hydrochloride |
| K2 | biphenyl-2,4-diamine hydrochloride |
| K3 | 2',4'-diaminobiphenyl-4-ol hydrochloride |
| K4 | 2',4'-diaminobiphenyl-3-ol hydrochloride |
| K11 | 1,3-diaminobenzene |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K15 | 3-amino-2-methylamino-6-methoxypyridine |
| K16 | 3,5-diamino-2,6-dimethoxypyridine dihydrochloride |
| K17 | 2,4-diamino-5-ethoxytoluene sulfate |
| K18 | N-(3-dimethylamino)phenylurea |
| K19 | 1,3-bis(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |
| K31 | 1,3-dihydroxybenzene |
| K32 | 2-methyl-1,3-dihydroxybenzene |

TABLE 4-continued

| | Couplers |
|---|---|
| K33 | 1-chloro-2,4-dihydroxybenzene |
| K34 | 4-(2'-hydroxyethyl)amino-1,2-methylenedioxy-benzene.HCl |
| K35 | 3,4-methylenedioxyphenol |
| K36 | 2-amino-5-methylphenol |

TABLE 5

Hair Colorants

| | Example No. | | | | | |
|---|---|---|---|---|---|---|
| | 18 | 19 | 20 | 21 | 22 | 23 |
| Dyes | (Dyes in grams) | | | | | |
| K1 | 0.1 | 0.12 | 0.05 | 0.07 | 0.10 | 0.12 |
| E8 | 0.30 | | | | | |
| E9 | | | | | 0.25 | 0.3 |
| E15 | | 0.25 | 0.3 | 0.25 | | |
| K12 | | | 0.05 | | | |
| K13 | | | | 0.05 | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring results | blond | blond | blond | blond | blond | blond |

| | Example No. | | | | | |
|---|---|---|---|---|---|---|
| | 24 | 25 | 26 | 27 | 28 | 29 |
| Dyes | (Dyes in grams) | | | | | |
| K2 | 0.1 | 0.12 | 0.05 | 0.07 | 0.10 | 0.12 |
| E8 | 0.30 | | | | | |
| E9 | | | | | 0.25 | 0.3 |
| E15 | | 0.25 | 0.3 | 0.25 | | |
| K12 | | | 0.05 | | | |
| K13 | | | | 0.05 | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring results | blond | blond | blond | blond | blond | blond |

| | Example No. | | | | | |
|---|---|---|---|---|---|---|
| | 30 | 31 | 32 | 33 | 34 | 35 |
| Dyes | (Dyes in grams) | | | | | |
| K3 | 0.1 | 0.12 | 0.05 | 0.07 | 0.10 | 0.12 |
| E8 | 0.30 | | | | | |
| E9 | | | | | 0.25 | 0.3 |
| E15 | | 0.25 | 0.3 | 0.25 | | |
| K12 | | | 0.05 | | | |
| K13 | | | | 0.05 | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring results | blond | blond | blond | blond | blond | blond |

| | Example No. | | | | | |
|---|---|---|---|---|---|---|
| | 36 | 37 | 38 | 39 | 40 | 41 |
| Dyes | (Dyes in grams) | | | | | |
| K4 | 0.1 | 0.12 | 0.05 | 0.07 | 0.10 | 0.12 |
| E8 | 0.30 | | | | | |
| E9 | | | | | 0.25 | 0.3 |
| E15 | | 0.25 | 0.3 | 0.25 | | |
| K12 | | | 0.05 | | | |
| K13 | | | | 0.05 | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring results | blond | blond | blond | blond | blond | blond |

Examples 42 to 65

Hair Colorants

Dye carriers in cream form and having the following composition were prepared:

| | |
|---|---|
| X g | of (1,1'-biphenyl)-2,4-diamine (coupler K1 to K4 of formula (I) as per Table 4) |
| U g | of developer E8 to E15 as per Table 2 |
| Y g | of coupler K11 to K36 as per Table 4 |
| Z g | of direct dye D2 as per Table 3 |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100.0 g | water |

Just before use, 30 g of the foregoing coloring cream was mixed with 30 g of a 6% aqueous solution of hydrogen peroxide. The mixture was then applied to the hair. After an exposure time of 30 min at 40° C., the hair was rinsed with water, washed with a commercial shampoo and dried. The coloring results are presented in Table 6.

TABLE 6

Hair Colorants

| | Example No. | | | | | |
|---|---|---|---|---|---|---|
| | 42 | 43 | 44 | 45 | 46 | 47 |
| Dyes | (Dyes in grams) | | | | | |
| K1 | 0.6 | 1.3 | 1.15 | 0.15 | 0.15 | 0.15 |
| E8 | 1.5 | | | | | |
| E13 | | 1.6 | | | | 0.7 |
| E15 | | | 1.8 | 0.7 | 0.7 | |
| K12 | 0.6 | | | | | |
| K31 | 1.10 | 1.10 | 1.10 | 0.40 | 0.40 | 0.40 |
| K23 | | | 0.05 | 0.10 | 0.10 | 0.10 |
| D2 | | | | 0.10 | 0.10 | 0.10 |
| Coloring results | black | black | black | brown | brown | brown |

| | Example No. | | | | | |
|---|---|---|---|---|---|---|
| | 48 | 49 | 50 | 51 | 52 | 53 |
| Dyes | (Dyes in grams) | | | | | |
| K2 | 0.6 | 1.3 | 1.15 | 0.15 | 0.15 | 0.15 |
| E8 | 1.5 | | | | | |
| E13 | | 1.6 | | | | 0.7 |
| E15 | | | 1.8 | 0.7 | 0.7 | |
| K12 | 0.6 | | | | | |

TABLE 6-continued

| Hair Colorants | | | | | | |
|---|---|---|---|---|---|---|
| K31 | 1.10 | 1.10 | 1.10 | 0.40 | 0.40 | 0.40 |
| K23 | | 0.05 | | 0.10 | 0.10 | 0.10 |
| D2 | | | | 0.10 | 0.10 | 0.10 |
| Coloring results | black | black | black | brown | brown | brown |

| | Example No. | | | | | |
|---|---|---|---|---|---|---|
| Dyes | 54 | 55 | 56 | 57 | 58 | 59 |
| | (Dyes in grams) | | | | | |
| K3 | 0.6 | 1.3 | 1.15 | 0.15 | 0.15 | 0.15 |
| E8 | 1.5 | | | | | |
| E13 | | 1.6 | | | | 0.7 |
| E15 | | | 1.8 | 0.7 | 0.7 | |
| K12 | 0.6 | | | | | |
| K31 | 1.10 | 1.10 | 1.10 | 0.40 | 0.40 | 0.40 |
| K23 | | 0.05 | | 0.10 | 0.10 | 0.10 |
| D2 | | | | 0.10 | 0.10 | 0.10 |
| Coloring results | black | black | black | brown | brown | brown |

| | Example No. | | | | | |
|---|---|---|---|---|---|---|
| Dyes | 60 | 61 | 62 | 63 | 64 | 65 |
| | (Dyes in grams) | | | | | |
| K4 | 0.6 | 1.3 | 1.15 | 0.15 | 0.15 | 0.15 |
| E8 | 1.5 | | | | | |
| E13 | | 1.6 | | | | 0.7 |
| E15 | | | 1.8 | 0.7 | 0.7 | |
| K12 | 0.6 | | | | | |
| K31 | 1.10 | 1.10 | 1.10 | 0.40 | 0.40 | 0.40 |
| K23 | | 0.05 | | 0.10 | 0.10 | 0.10 |
| D2 | | | | 0.10 | 0.10 | 0.10 |
| Coloring results | black | black | black | brown | brown | brown |

The invention claimed is:

1. Agent for oxidative dyeing of keratin fibers, said agent comprising at least one developer and at least one coupler, and wherein said at least one coupler comprises at least one (1,1'-biphenyl)-2,4-diamine derivative compound of formula (I), or a physiologically tolerated salt thereof:

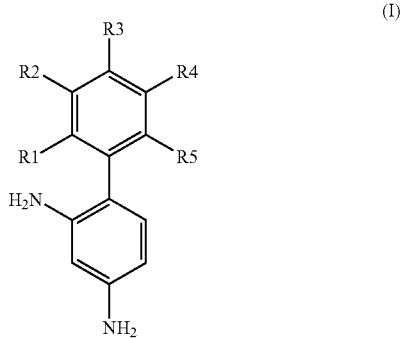

(I)

wherein R1, R2, R3, R4 and R5 can be equal or different and independently of each other, denote hydrogen, a halogen atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group, a $C_1$–$C_4$-monoalkylamino group, a di($C_1$–$C_4$)-alkylamino group, a trifluoromethyl group, a —C(O)H group, a —C(O)CH$_3$ group, a —C(O)CF$_3$ group, an —Si(CH$_3$)$_3$ group, a $C_1$–$C_4$-hydroxyalkyl group, a $C_2$–$C_4$-dihydroxyalkyl group, a —CH=CHR6 group, a —(CH$_2$)$_p$CO$_2$R7 group or a —(CH$_2$)$_p$R8 group with p=1, 2, 3 or 4, a —C(R9)=NR10 group or a —C(R12)H—NR13R14 group, or two adjacent ones of said R1, R2, R3, R4 and R5 together form an —O—CH$_2$—O— bridge;

R6 denotes hydrogen, a nitro group, a —CO$_2$R7 group or a —C(O)CH$_3$ group;

R7, R9 and R12 are the same or different and, independently of each, other denote hydrogen or a $C_1$–$C_4$-alkyl group;

R8 denotes an amino or nitrile group;

R10, R13 and R14 are the same or different and, independently of each other, denote hydrogen, a hydroxyl group, a $C_1$–$C_4$-alkyl group, a $C_1$–$C_4$-hydroxyalkyl group, a $C_2$–$C_4$-dihydroxyalkyl group or a group of the following formula (III)

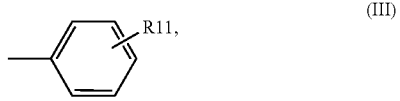

(III)

and R11 denotes hydrogen, an amino group or a hydroxyl group with a proviso that when R3=NH$_2$, and R$_1$=R$_2$=R$_4$=H, R$_5$ is not hydrogen.

2. Agent according to claim 1, wherein at least three of said R1, R2, R3, R4 and R5 denote hydrogen.

3. Agent according to claim 1, wherein three of said R1, R2, R3, R4 and R5 denote hydrogen and a remaining two of said R1, R2, R3, R4 and R5, independently of each other, denote hydrogen, a methoxy group, a hydroxyl group, a $C_1$–$C_4$-alkyl group, a $C_1$–$C_4$-hydroxyalkyl group or an amino group, or, when said remaining two of said R1, R2, R3, R4 and R5 are adjacent to each other, said remaining two of said R1, R2, R3, R4 and R5 together form said —O—CH$_2$—O— bridge.

4. Agent according to one claim 1, wherein said at lest one (1,1'-biphenyl)-2,4-diamine derivative compound of formula (I) is selected from the group consisting of biphenyl-2,4-diamine; 4-benzo-[1,3]-dioxol-5-ylbenzene-1,3-diamine; 4'-hydroxybiphenyl-2,4-diamine; 4'-aminobiphenyl-2,4-diamine; 3'-hydroxybiphenyl-2,4-diamine and 4'-methoxybiphenyl-2,4-diamine.

5. Agent according to claim 1, wherein said at least one (1,1'-biphenyl)-2,4-diamine devirative compound of formula (I) is present in an amount from 0.005 to 20 weight percent.

6. Agent according to claim 1, having a pH from 6.5 to 11.5.

7. Agent according to claim 1, wherein said at lest one developer is selected from the group consisting of 1,4-diaminobenzene, 1,4-diamino-2-methylbenzene, 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl; 1,4-diamino-2-methoxymethylbenzene, 1,4-diamino-2-aminomethylbenzene, 1,4-diamino-2-hydroxymethyl-benzene, 1,4-diamino-2-(2-hydroxyethoxy)benzene, 2-[2-(acetylamino)ethoxy]-1,4-diaminobenzene, 4-phenylaminoaniline, 4-dimethylaminoaniline, 4-diethyl-aminoaniline, 4-dipropylaminoaniline, 4-[ethyl-(2-hydroxyethyl)amino]aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(2-hydroxyethyl)benzene, 1-(2,5-diaminophenyl)-ethanol, 1,4-diamino-2-(1-methylethyl)benzene, 1,3-bis-[(4-aminophenyl)(2-hydroxyethyl)amino]-2-propanol, 1,4-bis-[(4-aminophenyl)amino]butane, 1,8-bis-(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-methyl-1H-pyrazole, 2-aminophenol, 2-amino-6-methylphenol and 2-amino-5-methylphenol.

8. Agent according to claim 1, containg said at least one coupler and said at least one developer in a total amount of 0.005 to 20 weight percent.

9. Agent according to claim 1, further comprising at least one direct-dyeing dye compound.

10. Agent according to claim 1, cosisting of a hair colorant composition.

11. A (1,1'-biphenyl)-2,4-diamine derivative of general formula (II), or a physiologically tolerated salt thereof:

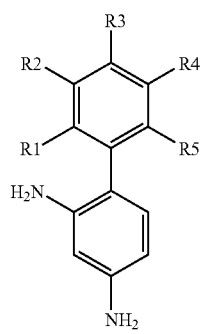

(II)

wherein R1, R2, R3, R4 and R5 are the same or different and, independently of each other, denote hydrogen, a chlorine atom, a fluorine atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkyl thioether group, a mercapto group, a nitro group, an amino group, a $C_1$–$C_4$-monoalkylamino group, a di($C_1$–$C_4$)-alkylamino group, a trifluoromethyl group, a —C(O)H group, a —C(O)CH$_3$ group, a —C(O)CF$_3$ group, an —Si(CH$_3$)$_3$ group, a $C_1$–$C_4$-hydroxyalkyl group, a $C_2$–$C_4$-dihydroxyalkyl group, a —CH=CHR6 group, a —(CH$_2$)$_p$—CO$_2$R7 group or a (CH$_2$)$_p$R8 group with p=1, 2, 3 or 4, a —C(R9)=NR10 group or a —C(R12)H—NR13R14 group, or two adjacent ones of said R1, R2, R3, R4 and R5 together form an —O—CH$_2$—O— bridge;

R6 denotes hydrogen, a nitro group, a —CO$_2$R7 group or a —C(O)CH$_3$ group;

R7, R9 and R12 are the same or different and, independently of each other, denote hydrogen or a $C_1$–$C_4$-alkyl group;

R8 denotes an amino group or a nitrile group;

R10, R13 and R14 are the same or different and, independently of each other, denote hydrogen, a hydroxyl group, a $C_1$–$C_4$-alkyl group, a $C_1$–$C_4$-hydroxyalkyl group, a $C_2$–$C_4$-dihydroxyalkyl group or a group of the following formula (III)

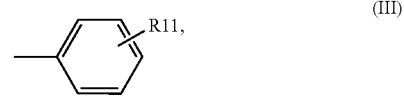

(III)

and R11 denotes hydrogen, an amino group or a hydroxyl group;

with the proviso that (i) at least one of said R1, R2, R3, R4 and R5 does not denote hydrogen; (ii) when R3=R5=NH$_2$, at least one of the said R1, R2 and R4 is different from hydrogen, (iii) when R1=R5=H, and R2=R4=tert-butyl, said R3 does not denote an OH group, (iv) when R2=R3=NH$_2$, at least one of said R1, R4 and R5 groups is different from hydrogen, (v) when R3=NH$_2$ and R1=R2=R4=H, R5 is not hydrogen, (vi) when R3=NH$_2$ and R5=H, at least one of R4, R2 and R1 is not hydrogen, and (vii) when R3=R4=NH$_2$, then at least one of said R1, R2 and R5 is different from hydrogen.

* * * * *